United States Patent [19]
Bahrmann et al.

[11] Patent Number: 5,463,147
[45] Date of Patent: Oct. 31, 1995

[54] DECYL ALCOHOL MIXTURES, PHTHALIC ESTERS OBTAINABLE THEREFROM AND THEIR USE AS PLASTICIZERS

[75] Inventors: Helmut Bahrmann, Hamminkeln; Wolfgang Greb, Dinslaken; Peter Heymanns, Essen; Peter Lappe; Thomas Müller, both of Dinslaken; Jürgen Szameitat, Wesel; Ernst Wiebus, Oberhausen, all of Germany

[73] Assignee: Hoechst Aktiengesellschaft, Germany

[21] Appl. No.: 311,561

[22] Filed: Sep. 23, 1994

[30] Foreign Application Priority Data

Sep. 30, 1993 [DE] Germany ............... 43 33 324.9

[51] Int. Cl.⁶ .................. C07C 27/22; C07C 29/141; C07C 31/125
[52] U.S. Cl. .................. 568/882; 524/296; 560/76; 568/452; 568/453; 568/883
[58] Field of Search .................. 568/452, 453, 568/882, 883

[56] References Cited

U.S. PATENT DOCUMENTS

| | | | |
|---|---|---|---|
| 4,426,542 | 1/1984 | Barker et al. | 568/883 |
| 4,447,661 | 5/1984 | Hoshiyama et al. | 568/884 |
| 4,684,750 | 8/1987 | Kessen et al. | 568/882 |
| 5,189,105 | 2/1993 | Miyazawa et al. | 560/76 |
| 5,268,514 | 12/1993 | Bahrmann et al. | 568/882 |
| 5,369,162 | 11/1994 | Bahrmann et al. | 560/76 |

FOREIGN PATENT DOCUMENTS

| | | |
|---|---|---|
| 94456 | 11/1983 | European Pat. Off. . |
| 562451 | 9/1993 | European Pat. Off. . |
| 1165568 | 3/1964 | Germany . |
| 3232557 | 3/1983 | Germany . |
| 614010 | 12/1948 | United Kingdom . |

*Primary Examiner*—Joseph E. Evans
*Attorney, Agent, or Firm*—Jordan B. Bierman; Bierman and Muserlian

[57] ABSTRACT

Mixtures of isomeric decyl alcohols prepared by hydroformylation of mixtures of butene-1 and butene-2 in two stages to give aldehyde mixtures, and condensation of the aldehyde mixtures to form an aldol mixture, followed by separation and hydrogenation. The first stage of the hydroformylation proceeds in the presence of rhodium catalysts dissolved in water, the second stage in the presence of cobalt catalysts homogeneously dissolved in the reaction medium. The mixture of isomeric decyl alcohols, when esterified with phthalic acid, yields a mixture of isomeric decyl phthalates which are useful as plasticizers.

8 Claims, No Drawings

DECYL ALCOHOL MIXTURES, PHTHALIC ESTERS OBTAINABLE THEREFROM AND THEIR USE AS PLASTICIZERS

This Application claims the benefit of the priority of German Application P 43 33 324.9, filed Sep. 30, 1993.

The invention relates to mixtures of isomeric decyl alcohols, a process for their preparation, the phthalic esters obtained from these alcohols, and their use as plasticizers.

BACKGROUND OF THE INVENTION

Esters of phthalic acid are used to a great extent as plasticizers, in particular for polyvinylchloride. The alcohol components customarily used are primary aliphatic alcohols having 8 to 10 carbon atoms, among which 2-ethylhexanol currently is of the greatest importance. Phthalic esters of alcohols having less than 8 carbon atoms in the molecule lead to plasticizers having good gelling power. However, their relatively high volatility is a disadvantage. Phthalic esters which are derived from primary aliphatic alcohols having more than 10 carbon atoms, in contrast, gel more slowly and are less cold-resistant.

The properties of the phthalic ester plasticizers are influenced by the branching of the carbon chain, in addition to the size of the alcohol molecules. Thus, alcohols with a low degree of branching give ester plasticizers of high cold flexibility. Substantially linear alcohols having 8 to 10 carbon atoms in the molecule are therefore gaining increasing importance as the alcohol component of phthalic esters. A precondition for their use is that they be available in large amounts and at a reasonable cost.

According to German Patent 2 855 421, phthalates of 9 carbon alcohols, useful as plasticizers, are obtained by hydroformylation of 8 carbon olefins, hydrogenation of the reaction product, and esterification of the resultant 9 carbon alcohols with phthalic anhydride. 3% to 20% by weight of the starting olefins have an isobutane skeleton in each molecule chain, less than 3% by weight of the olefins has a quaternary carbon, and more than 90% by weight of the total amount of olefins is present as n-octenes, monomethylheptenes, and dimethylhexenes. In addition, the weight ratio of the total amount of n-octenes and monomethylheptenes to the dimethylhexenes is more than 0.8.

Phthalic esters of 10 carbon alcohols are the subject matter of European Patent Application 03 66 089. The alcohols used for the esterification are in the form of a mixture produced by hydroformylation of a butene fraction, aldol condensation of the resulting aldehyde mixture, and subsequent hydrogenation. The hydroformylation step, according to the process description, is not subject to any restrictions. Thus, not only cobalt, but also rhodium, can be used as catalyst, and the addition of an organic compound of trivalent phosphorus is not excluded.

Another way to obtain didecyl phthalic mixtures is described in European Patent Application 04 24 767. The esters are prepared by a multi-stage process by dimerization of butene mixtures, hydroformylation, and hydrogenation of the resulting octene mixture to a nonanol mixture, dehydration of the nonanol mixture to form a nonene mixture, followed by hydroformylation and hydrogenation of the nonene mixture to form a decanol mixture.

The known processes do not satisfy all of the requirements, both economic and technical, which are made of a process to be carried out on an industrial scale. The starting materials are either not available in sufficient quantities, or they are not inexpensive, or the conversion of the starting materials into the desired alcohols is associated with excessively complex (and hence costly) processes. In multi-stage processes, which include the hydroformylation of butene, the n-valeraldehyde content, in particular, of the hydroformylation product should be as high as possible, to promote the formation of straight-chain alcohols or alcohols which are only slightly branched.

SUMMARY OF THE INVENTION

The object was, therefore, to develop a process which not only starts from raw materials which are inexpensive and readily available, but which can also be converted in a scientifically simple manner into the desired straight-chain or only slightly branched alcohols.

The isomeric decyl alcohols of the present invention are obtained in two stages. First, olefin mixtures containing butene-1 and butene-2 are hydroformylated, the reaction proceeding in the first stage in a heterogeneous reaction system using, as catalysts, rhodium compounds containing complexed water-soluble phosphines. The first stage is carried out at temperatures of 70° to 150° C. and pressures of 0.4 to 30 MPa. In the second stage, the reaction of the product of the first stage takes place in a homogeneous phase, in the presence of cobalt compounds as catalysts, at temperatures of 130° to 180° C. and pressures of 8 to 30 MPa to form aldehyde mixtures. Separation and combination of the resulting aldehyde mixtures from the hydroformylation stages, condensation of the combined aldehyde mixture to form an aldol mixture, and separating and hydrogenating the aldol mixture provide the desired mixture of isomeric decyl alcohols.

DETAILED DESCRIPTION OF THE INVENTION

The 1-butene- and 2-butene-containing starting mixtures for the preparation of the isomeric decyl alcohols according to the invention are necessarily produced in large quantities as refinery by-products in the production of motor vehicle fuels and in the preparation of ethylene by thermal cracking of high molecular weight hydrocarbons. They are isolated from the 4 carbon cracking cuts of the pyrolysis product by extraction of the butadiene with a selective solvent and subsequent separation of the isobutene, preferably by conversion into methyl tert-butyl ether. The n-butene-containing product separated from the pyrolysis product which has been freed of butadiene is termed raffinate I. If, in addition, the isobutene is separated with the n-butene, the product is called raffinate II. Instead of extracting butadiene, it can be partially hydrogenated in the 4 carbon cracking cut to give butenes. After separating out the i-butene, a butene-1/butene-2 mixture is obtained which is particularly suitable for further processing to 10 carbon alcohols. Finally, attempts have been made recently to hydrogenate the separated butadiene to form butane and return it to the cracking vessel to increase the yield of ethylene and propylene.

According to the invention, mixtures containing butene-1 and butene-2, e.g. in the form of raffinate II, but which may also be of different origin and composition, are hydroformylated in two stages. In the first stage, butene-1 preferably reacts to form a mixture which predominantly comprises n-valeraldehyde and, in a lesser amount, i-valeraldehyde. The reaction proceeds under conditions which largely exclude an isomerization of the butene-1 to give butene-2. In the second stage, the butene-2 is hydroformylated to give a mixture of n-valeraldehyde and i-valeraldehyde.

The first stage of the hydroformylation is carried out as a heterogeneous reaction in a two-phase system, a conversion which is described, e.g. in DE-C 26 27 354. This process is characterized by the presence of an organic phase, which contains the starting olefins and the reaction product, and an aqueous phase, in which the catalyst is dissolved. The catalysts which are used are water-soluble rhodium complex compounds which contain water-soluble phosphines as ligands. The phosphines include, in particular, triarylphosphines, trialkylphosphines, and arylated or alkylated diphosphines, the organic radicals of which are substituted by sulfonic acid groups or carboxyl groups. Their preparation is disclosed by, e.g. DE-C 26 27 354 and German Democratic Republic patent 259 194.

The butene reaction proceeds at temperatures of 70° to 150° C., preferably 100° to 130° C. and at pressures of from 0.4 to 30, in particular 1 to 10, MPa with water gas which contains carbon monoxide and hydrogen in a volume ratio of 1:10 to 10:1. The rhodium concentration is 20 to 1000 ppm by weight, preferably 50 to 500 ppm by weight, based on the aqueous catalyst solution. Per mole of rhodium, 4 to 100 mol of water-soluble phosphine are used. The volume ratio of aqueous to organic phase is 0.1 to 10:1.

The conversion of butene per unit of time is markedly increased if a phase transfer reagent (solubilizer) is added to the aqueous catalyst solution. It alters the physical properties of the interfaces between the two liquid phases and facilitates the transfer of the organic reactant into the aqueous catalyst phase.

Known solubilizers are compounds whose hydrophilic groups are anionic, cationic, or nonionic. The anionic compounds include sodium salts, potassium salts, or ammonium salts of carboxylic acids having 8 to 20 carbon atoms, in particular of saturated fatty acids having 12 to 18 carbon atoms, as well as alkyl sulfates, alkylbenzenesulfonates, and alkylbenzenephosphonates. Examples of cationic solubilizers are tetraalkylammonium and N-alkylpyridinium salts. The nonionic phase transfer reagants cannot dissociate into ions in aqueous solution. They include alkyl polyethylene glycols, alkylphenyl polyethylene glycols, alkylolamides of fatty acids, and trialkylamine oxides. Finally, ampholytes such as aminocarboxylic acids, betaines, and sulfobetaines are also useful as solubilizers.

Cationic solubilizers, in particular of the formula $[A-N(R^1R^2R^3)]^+E^-$ have proven to be useful. A is a straight or branched chain alkyl radical having 6 to 25 carbon atoms, $R^1$, $R^2$, and $R^3$ are the same or different and are straight or branched chain alkyl radicals having 1 to 5 carbon atoms, and E is an anion, in particular sulfate, tetrafluoroborate, acetate, methosulfate, benzenesulfonate, alkylbenzenesulfonate, toluenesulfonate, lactate, or citrate.

In the first reaction stage, hydroformylation of the butene-1 contained in the butene mixture to n-valeraldehyde should be as complete as possible. A decisive criterion for the termination of the reaction is the increased production of i-valeraldehyde. Its content should be less than 10% by weight (based on the aldehyde mixture). Thus, for a butene-1 conversion rate which, depending on the reaction parameters selected, is up to 95%, the aldehyde mixture contains at least 90% n-valeraldehyde, the rest is i-valeraldehyde.

Olefins which did not react in the first stage (predominantly butene-2) leave the reactor together with carbon monoxide, hydrogen, and the butane formed by hydrogenation of the olefins. The gas mixture is subjected to a pressure of 8 to 30 MPa without intermediate treatment and is further reacted in a homogeneous phase in a second reaction stage at temperatures of 130° to 180° C. The catalyst used is cobalt. It is fed to the reaction mixture as the metal, expediently in a finely divided form, or better as a compound soluble in organic media, e.g. as cobalt carbonyl or as a salt of a carboxylic acid, such as 2-ethylhexanoic acid. The cobalt concentration is 0.1% to 3% by weight, preferably 0.6% to 1.0% by weight, based on the butenes introduced into the second reaction stage. The presence of a solvent such as toluene, xylene, or tetrahydrofuran is not absolutely necessary, because its function can be taken over by the starting material and the reaction product. The water gas has the same composition as in the first reaction step. Depending on the reaction conditions, up to 99% of the olefin used is converted into n- and i-valeraldehyde.

After termination of each hydroformylation, the aldehyde mixtures of each of the reaction steps are separated off from their respective catalysts, from the unreacted starting materials, and from the remaining products. In the case of the heterogeneous reaction (first stage), this is carried out by simple phase separation. For the reaction in homogeneous phase, i.e. the second stage of the novel process, the catalyst is removed from the depressurized or partly depressurized reaction product by known processes, e.g. by treatment with steam (cf. DE-C-3 032 252).

The aldol condensation of the combined aldehyde mixtures of the first and second hydroformylation stages is carried out in a conventional manner under the action of basic catalysts. Pretreatment of the aldehydes, e.g. special purification, is not required. Catalysts which are used include alkali metal carbonates or alkali metal hydroxides, in particular compounds of sodium, potassium, or amines, preferably tertiary amines, such as triethylamine, tri-n-propylamine, and tri-n-butylamine. The reaction is carried out at temperatures of 60° to 160° C., in particular 80° to 130° C., under atmospheric or elevated pressure up to about 1 MPa. The reaction time is from a few minutes up to several hours and is dependent, in particular, on the catalyst type and reaction temperature. Owing to its higher reaction velocity, n-valeraldehyde preferentially aldolizes with itself or with isomeric valeraldehydes to give decenals; any condensation of 2-methylvaleraldehyde or isovaleraldehyde, in contrast, is so minimal as to be insignificant.

The aldehyde mixture obtained by the foregoing condensation is then hydrogenated to give the desired decyl alcohol mixture. The addition of hydrogen proceeds in a known manner in the presence of catalysts. Those which are suitable are, for example, hydrogenation catalysts based on nickel, chromium, or copper. The hydrogenation temperature is conventionally between 100° and 180° C. and the pressure between 1 and 10 MPa. The decyl alcohol mixture is purified by distillation and is especially suitable as the alcohol component of phthalic esters which are to be used as plasticizers.

The preparation of the phthalic esters is known [cf. Ullmann, Encyclopädie der Technischen Chemie [Encyclopedia of Industrial Chemistry] (1979), Vol. 18, pages 536 et seq.]. Phthalic anhydride is expediently reacted in one stage with the decyl alcohol mixture in the molar ratio 1:2. The reaction velocity can be increased by catalysts and/or by increasing the reaction temperature. In order to shift the equilibrium in the direction of ester formation, it is necessary to remove the resulting water from the reaction mixture. The phthalates obtained from the decyl alcohol mixture according to the invention are distinguished as plasticizers by excellent cold properties.

While only a limited number of specific embodiments of the present invention have been expressly disclosed, it is, nonetheless, to be broadly construed and not to be limited except by the character of the claims appended hereto.

What we claim is:

1. An alcohol mixture of isomeric decyl alcohols which is the product of hydroformylation of an olefinic mixture containing butene-1 and butene-2, said hydroformylation being carried out in a first stage and a second stage, said first stage comprising a first hydroformylation of said olefin mixture in a heterogeneous reaction system at a first temperature of 70° to 150° C. and under a first pressure of 0.4 to 30 MPa in the presence of an aqueous solution of a first catalyst, said first catalyst comprising at least one rhodium compound and at least one water-soluble phosphine, to form a first reaction mixture containing a first aldehyde mixture, separation of said first aldehyde mixture from said first reaction mixture leaving a residue which contains butene-2, said second stage comprising a second hydroformylation of said residue in a homogeneous reaction system at a second temperature of 130° to 180° C. and under a second pressure of 8 to 30 MPa in the presence of a cobalt catalyst to form a second reaction mixture containing a second aldehyde mixture, separation of said second aldehyde mixture from said second reaction mixture, combination of said first aldehyde mixture with said second aldehyde mixture to form a combined aldehyde mixture, condensation of said combined aldehyde mixture to form a third reaction mixture containing an aldol mixture, separation of said aldol mixture from said third reaction mixture, and hydrogenation of said aldol mixture to form said alcohol mixture.

2. The alcohol mixture of claim 1 wherein said first temperature is 100° to 130° C. and said first pressure is 1 to 10 MPa.

3. The alcohol mixture of claim 1 wherein said first catalyst is present in a first catalyst amount of 20 to 1000 ppm by weight, based on said aqueous solution.

4. The alcohol mixture of claim 3 wherein said first catalyst amount is 50 to 500 ppm by weight.

5. The alcohol mixture of claim 1 wherein said first catalyst, per mol of rhodium, contains 4 to 100 mol of said water-soluble phosphine.

6. The alcohol mixture of claim 1 wherein said aqueous solution contains a transfer reagent.

7. The alcohol mixture of claim 1 wherein said cobalt catalyst comprises 0.1% to 3% by weight of cobalt, based on said butenes in said second hydroformylation.

8. The alcohol mixture of claim 7 wherein said cobalt catalyst comprises 0.6% to 1.0% by weight of cobalt.

* * * * *